United States Patent [19]

Naumann

[11] Patent Number: 5,353,453
[45] Date of Patent: Oct. 11, 1994

[54] TANNING TOWEL WITH REFLECTIVE SURFACE

[76] Inventor: Mary D. Naumann, 4048 Plumbrook Dr., Toledo, Ohio 43623

[21] Appl. No.: 103,284

[22] Filed: Aug. 6, 1993

[51] Int. Cl.⁵ ............................................. A47G 9/06
[52] U.S. Cl. .................... 5/417; 5/922/420; 428/285; 428/938
[58] Field of Search ...................... 5/417–420, 5/482, 922, 923; 428/938, 285

[56] References Cited

U.S. PATENT DOCUMENTS

| | | | |
|---|---|---|---|
| 2,870,464 | 1/1959 | Lalick | 5/420 |
| 4,032,681 | 6/1977 | Jonnes | 428/253 |
| 4,097,944 | 7/1978 | Yulish | 5/419 |
| 4,738,545 | 4/1988 | Writgor | 5/420 |
| 4,776,043 | 10/1988 | Coleman | 2/199 |
| 4,918,758 | 4/1990 | Rendina | 2/171 |
| 4,951,333 | 8/1990 | Kaiser et al. | 5/417 |
| 4,975,987 | 12/1990 | Teachout | 2/246 |
| 5,003,640 | 4/1991 | Pizzacar | 2/199 |
| 5,010,590 | 4/1991 | Haber et al. | 2/12 |
| 5,018,230 | 5/1991 | Steberger | 5/420 |
| 5,052,056 | 10/1991 | Braun | 2/115 |
| 5,091,994 | 3/1992 | Delane | 2/195 |
| 5,136,726 | 8/1992 | Kellin | 2/244 |

FOREIGN PATENT DOCUMENTS

| | | | |
|---|---|---|---|
| 2431271 | 3/1980 | France | 5/417 |
| 2481588 | 11/1981 | France | 5/417 |
| 2431271 | 2/1989 | France . | |

*Primary Examiner*—Alexander Grosz
*Attorney, Agent, or Firm*—Willian Brinks Hofer Gilson & Lione

[57] ABSTRACT

A tanning towel is disclosed which is capable of enhancing suntanning by having a reflective side made of a pliable fabric which can be washed and dried in a normal fashion and which can be attached to a conventional towel using a hook-and-loop (Velcro) type attachment or stitching.

9 Claims, 2 Drawing Sheets

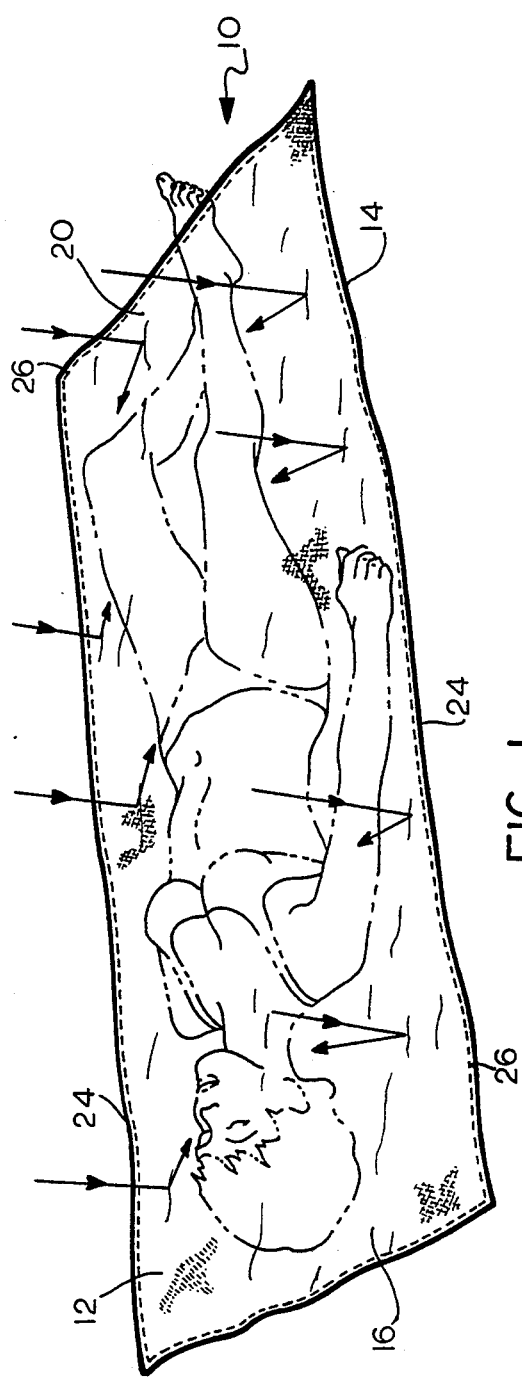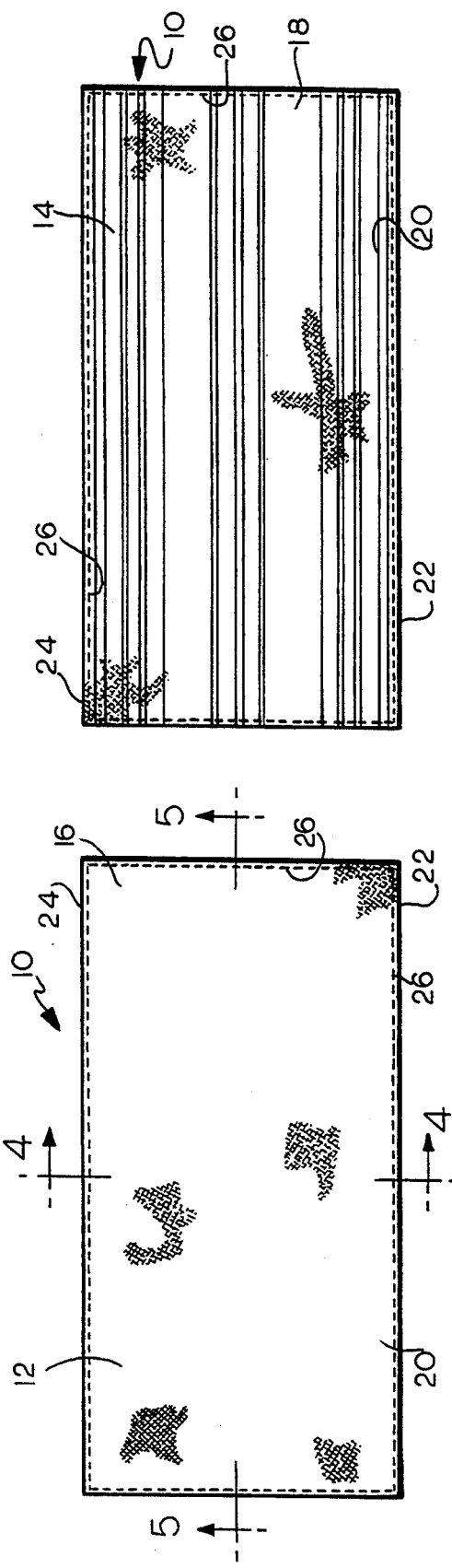

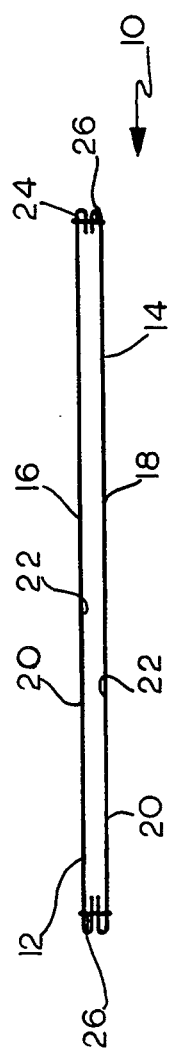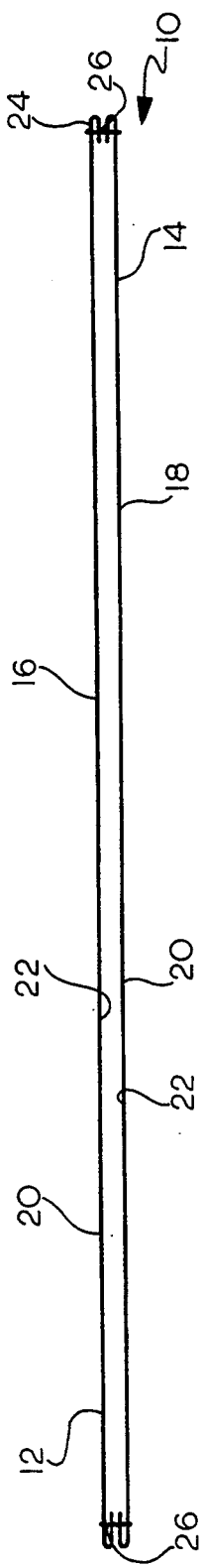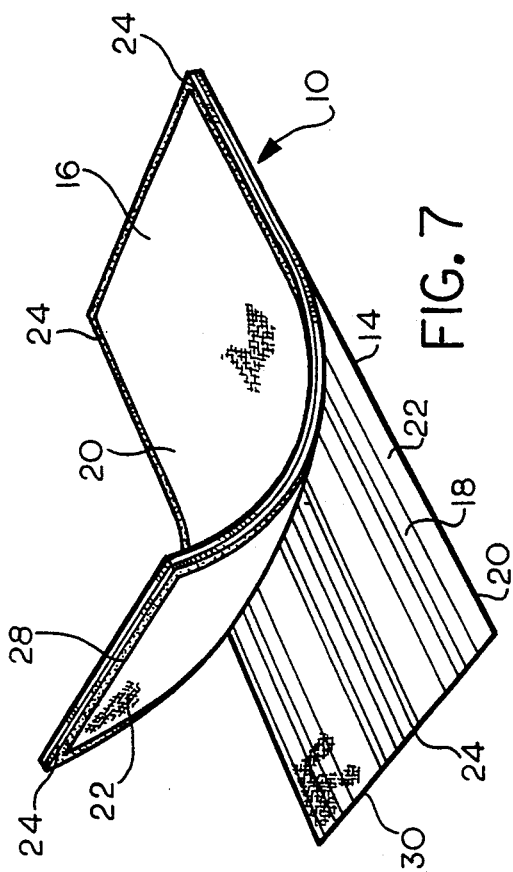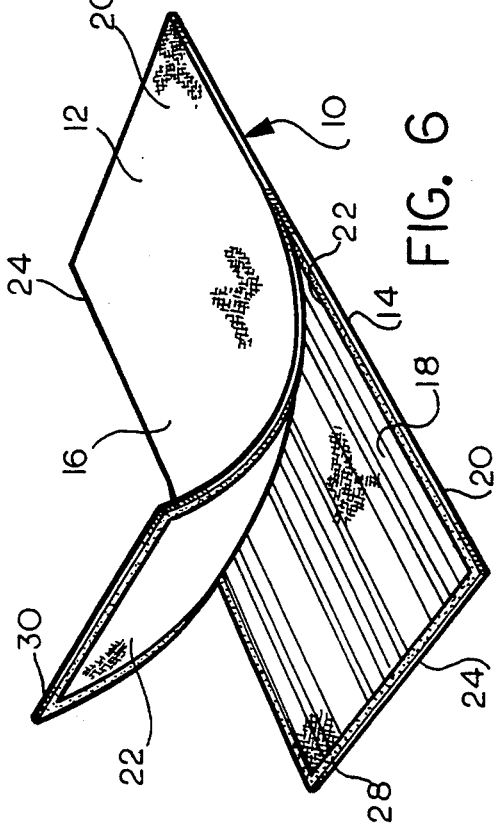

TANNING TOWEL WITH REFLECTIVE SURFACE

FIELD OF THE INVENTION

This invention relates to towels, blankets and the like which are used to enhance the tanning of a sunbather.

BACKGROUND OF THE INVENTION

Sunbathers often lie on a towel, mat, lounge chair, or the like when in the sun. Such a base provides protection from the surface, often sand on a beach, and, perhaps to a lesser extent, a cushion for more comfortable reclining. Many sunbathers also desire to enhance the amount of sunlight incident upon their bodies while lying in the sun. This is done by using various means for reflecting nearby sunlight onto their body. The various means for reflecting sunlight onto a sunbathers body typically employ a type of metallic foil attached to the towel, mat, or the like. For example, U.S. Pat. No. 2,675,807 (Pursel) shows a blanket with a fabric backing having a plurality of metallic foil (such as aluminum foil) strips attached to it to reflect rays of light. U.S. Pat. No. 4,476,593 (Faneslow) also shows a blanket which consists of a substrate having a plurality of aluminum (or tin oxide) coated incremental reflectors in a Fresnel pattern. The suntanning mats disclosed in U.S. Pat. Nos. 3,902,753 (Wilson) and No. 4,518,198 (Daniels) also show reflective surfaces having a metallic foil.

The surfaces noted above, however, are delicate and cannot easily withstand normal wear and tear at the beach or other locations frequented by sunbathers. In addition, these blankets and mats are not readily washable in conventional washers and dryers, nor are they easily useable for the purpose of drying off. Further, the means used to attach the reflective surfaces in these devices do not easily allow them to be removed if necessary. Moreover, these devices are concerned mainly with the single purpose of maximizing the amount of sunlight reflected onto the sunbather's body to the exclusion of any other practical purposes.

While hook and loop materials (more commonly known as Velcro, registered trademark) have been used as a means of closure or of fastening objects, especially apparel, none of the previously mentioned devices use such a structure for fastening a pliable reflective surface to a towel to enhance suntanning.

Accordingly, one aspect of the present invention is to provide a versatile tanning towel which can be used for normal towel functions, such as drying and cleaning, while also capable of functioning as a reflective surface to enhance suntanning. More particularly, it is an aspect of the present invention to provide a towel having a side for normal towel functions and a side for suntanning. A further aspect of the present invention is to provide a towel capable of enhancing suntanning and being cleaned in conventional washing and drying machines. It is a further aspect of the present invention to provide a towel capable of enhancing suntanning and being folded or bunched without affecting the reflective properties of the reflective surface. Yet another aspect of the present invention is to provide a suntanning towel which is simple to manufacture and easy to use. Still another aspect is to provide a towel capable of enhancing suntanning without using metallic or foil type surfaces to reflect the sun's rays.

SUMMARY OF THE INVENTION

Briefly, according to this invention there is provided a versatile tanning towel which can be used for normal towel functions, such as drying and cleaning, which is also capable of functioning as a reflective surface to enhance suntanning. The suntanning towel includes a front surface and a back surface, wherein at least one of the surfaces is a light reflective, pliant fabric material. In a preferred embodiment the front surface is a light reflective, pliant fabric material and the back surface is a moisture-absorbent fabric material. The front surface and the back surface of the tanning towel may be of individual pieces of material wherein the front surface and the back surface each have a front face and a back face. The back face of the front surface and the back face of the back surface are attached to form a single towel.

The front surface and the back surface of the tanning towel may be attached by stitching along peripheral edges of the towel or the front surface and the back surface of the tanning towel may be attached by a hook-and-loop (Velcro) type attachment. In one embodiment of the present invention the front surface and the back surface of the tanning towel are attached by stitching along the length and width of the towel such that the stitching intersects at right angles to form square and rectangular sections on the face of the towel. In yet another embodiment of the present invention the front surface of the tanning towel has a strip of hooks attached along a perimeter of a back face of the front surface and the back surface has a strip of loops attached along a perimeter of a back face of the back surface such that the hooks and loops cooperatively releasably attach the front surface and the back surface to form a unitary tanning towel.

BRIEF DESCRIPTION OF THE DRAWINGS

Further features and other aspects and advantages of this invention will become clear from the following detailed description made with reference to the drawings in which:

FIG. 1 is a perspective view of a preferred embodiment of the present invention showing a sunbather lying on the invention;

FIG. 2 is a top view showing the reflective side of the present invention;

FIG. 3 is a top view showing a non-reflective side of the present invention;

FIG. 4 is a cut-away end view of the present invention along line 4—4 of FIG. 2 showing attachment of the two sheets;

FIG. 5 is a cut-away side view of the present invention along line 5—5 of FIG. 2 showing attachment of the two sheets;

FIG. 6 is a perspective view of the present invention showing a hook-and-loop (Velcro) type attachment on each of the two sheets forming the tanning towel; and FIG. 7 is a perspective view of the present invention showing the reflective sheet having a hook-and-loop (Velcro) type attachment on either side such that a towel can be attached to either side of the reflective sheet.

DESCRIPTION OF THE PREFERRED EMBODIMENTS

Referring to the drawings, wherein like reference characters represent like elements, FIGS. 1–7 illustrate a tanning towel 10 in accordance with the present invention.

The tanning towel 10 consists of a front surface 12 and a back surface 14 and may be made of a single sheet material 16 or, in a preferred embodiment, two sheet materials 16 and 18 secured together. At least one surface, 12 or 14, of a sheet, 16 and 18, of the tanning towel 10 is a pliable reflective surface to promote reflection of incident rays from the sun to aid in tanning.

As shown in FIGS. 2–7, the tanning towel 10 includes two sheets, 16 and 18, attached to one another. Sheets 16 and 18 are rectangular in shape and may be of any desirable dimension such as approximately 8 feet by 4 feet to accommodate a sunbather. Each individual sheet, 16 and 18, forming a front surface 12 and a back surface 14 of the tanning towel 10 has a front face 20 and a back face 22 and a peripheral edge 24. The sheets 16 and 18 may be attached to one another along the peripheral edge 24 by stitching 26, FIGS. 4 and 5. One of the sheets, shown in FIGS. 1–7 as sheet 16, has at least one reflective face 20. The reflective face 20 of sheet 16 consists preferably of a pliable nylon fabric, coated or colored with a reflective material such as silver or aluminum. In a preferred embodiment, sheet 16 is a nylon material of a type which may readily purchased in a fabric store. The other sheet, shown in FIGS. 1–7 as sheet 18, preferably is a conventional towel made of a cotton material such as terry cloth and the like.

An alternative embodiment of the present invention is shown in FIGS. 6 and 7. The two sheets 16 and 18 forming the tanning towel 10 are attached by a hook-and-loop type arrangement, more commonly referred to as Velcro (registered trademark). One sheet 16 has a strip of material 28 comprising a multiplicity of loops along the peripheral edges of a face 22 of the sheet. The strip 28 need not be continuous but can be intermittently placed along the peripheral edges 24 of the sheet face 22. The other sheet 18 has a strip of material 30 comprising a plurality of hooks correspondingly positioned for cooperating engagement with the strip of loops of 28 of the opposing sheet face 22. The strip of material 30 containing the hooks also need not be continuous but can be placed intermittently along the peripheral edges 24 of the sheet face 22. The interaction of the loops 28 on one sheet and the hooks 30 on the other sheet provide a means of releasably attaching the sheets together. It will be appreciated that by releasably attaching the sheets 16 and 18 of the tanning towel 10 to one another each sheet may be used and cleaned separately if desired. Furthermore, a tanning towel 10 incorporating a pliant reflective surface of nylon has the advantage of being machine washable and foldable without damaging the reflective properties of the tanning towel.

In use, as shown in FIG. 1, the tanning towel 10 is positioned with a reflective face 20 of the front surface 12 upward. The sunbather then is positioned atop the reflective face 20 of the towel 10 such that the reflective surface reflects sunlight onto the sunbather. However, because of the versatility of a tanning towel 10 made in accordance with the present invention, a sunbather has the option of using either the cloth surface 14 or reflective surface 12 of the tanning towel as desired.

It is to be understood that the present invention is not limited to the embodiments described above, but encompasses any and all embodiments within the scope of the following claims:

What is claimed is:

1. A suntanning towel comprising a front surface and a back surface, said front surface of a reflective, pliant fabric material and said back surface of a moisture-absorbent fabric material.

2. The towel of claim 1 wherein said front surface and said back surface are individual pieces of material, said front surface and said back surface each having a front face and back face, said front surface and said back surface attached to form a single towel.

3. The towel of claim 2 wherein said front surface and said back surface are attached by stitching along peripheral edges of said towel.

4. The towel of claim 2 wherein said front surface and said back surface are attached by stitching along the length and width of said towel, said stitching intersecting at right angles to from square and rectangular sections on said towel.

5. The towel of claim 2 wherein said front surface and said back surface are attached by a hook-and-loop (Velcro) type attachment, said front surface having a strip of hooks attached along a perimeter of a back face of said front surface, said back surface having a strip of loops attached along a perimeter of a back face of said back surface such that said hooks and loops cooperatively releasably attach said front surface and said back surface to form a unitary tanning towel.

6. A suntanning towel comprising a front surface and a back surface of individual pieces of material, said front surface and said back surface each having a front face and a back face, said front face of said front surface of a reflective, pliant fabric material and said front face of said back surface of a moisture-absorbent fabric material, said front surface and said back surface attached to form a single towel.

7. The towel of claim 6 wherein said front surface and said back surface are attached by stitching along peripheral edges of said towel.

8. The towel of claim 6 wherein said front surface and said back surface are attached by stitching along the length and width of said towel, said stitching intersecting at right angles to from square and rectangular sections on said towel.

9. The towel of claim 6 wherein said front surface and said back surface are attached by a hook-and-loop (Velcro) type attachment, said front surface having a strip of hooks attached along a perimeter of a back face of said front surface, said back surface having a strip of loops attached along a perimeter of a back face of said back surface such that said hooks and loops cooperatively releasably attach said front surface and said back surface to form a unitary tanning towel.

* * * * *